United States Patent
Malkov et al.

(10) Patent No.: US 8,999,139 B2
(45) Date of Patent: Apr. 7, 2015

(54) OXIDATION/REDUCTION MEASUREMENT

(75) Inventors: Vadim B. Malkov, Fort Collins, CO (US); David Langley Rick, Longmont, CO (US)

(73) Assignee: Hach Company, Loveland, CO (US)

(*) Notice: Subject to any disclaimer, the term of this patent is extended or adjusted under 35 U.S.C. 154(b) by 187 days.

(21) Appl. No.: 13/459,561

(22) Filed: Apr. 30, 2012

(65) Prior Publication Data
US 2012/0298529 A1    Nov. 29, 2012

Related U.S. Application Data

(63) Continuation-in-part of application No. PCT/US2011/038124, filed on May 26, 2011.

(51) Int. Cl.
G01N 27/26    (2006.01)
G01N 27/416   (2006.01)
G01N 33/18    (2006.01)

(52) U.S. Cl.
CPC .......... *G01N 27/4168* (2013.01); *G01N 33/182* (2013.01)

(58) Field of Classification Search
CPC ... G01N 27/10; G01N 27/26; G01N 27/4168; G01N 27/4163; G05D 21/02
USPC ................... 205/775, 778.5, 782; 436/50, 55; 702/22
See application file for complete search history.

(56) References Cited

U.S. PATENT DOCUMENTS

| | | |
|---|---|---|
| 4,713,772 A | 12/1987 | Carlson |
| 5,073,499 A | 12/1991 | Bellows |
| 5,978,746 A | 11/1999 | Beneteau et al. |
| 6,620,315 B2* | 9/2003 | Martin ......................... 210/96.1 |
| 7,155,971 B2 | 1/2007 | Wamhof et al. |
| 8,364,229 B2* | 1/2013 | Simpson et al. .............. 600/345 |
| 2007/0060785 A1* | 3/2007 | Freeman et al. ................ 600/16 |
| 2008/0034845 A1 | 2/2008 | Morris |

FOREIGN PATENT DOCUMENTS

| | | |
|---|---|---|
| JP | 2008-184838 A | 8/2008 |
| WO | 94-20825 A1 | 9/1994 |
| WO | 97-26606 A1 | 7/1997 |

OTHER PUBLICATIONS

"PID Without a PhD", Tim Wescott, accessed Oct. 23, 2009.*
International Searching Authority (EPO), Search Report for International Application PCT/US2012/039339, Sep. 10, 2012, 2 pages.
International Searching Authority (EPO), Search Report for International Application PCT/US2011/038124, Dec. 27, 2011, 2 pages.

* cited by examiner

Primary Examiner — Alex Noguerola
Assistant Examiner — Steven Rosenwald
(74) Attorney, Agent, or Firm — Ference & Associates LLC (57) ABSTRACT

Oxidation/reduction measurement is described. An aspect provides an oxidation/reduction quantification method, including: receiving intermittent oxidizer/reducer reference measurements from one or more reference sensors; receiving one or more substantially continuous oxidizer/reducer-related measurements from one or more corroboration sensors; and processing the one or more substantially continuous oxidizer/reducer-related measurements with the intermittent oxidizer/reducer reference measurements to generate substantially continuous representative oxidizer/reducer measurements. Other aspects are described.

7 Claims, 7 Drawing Sheets

OXIDATION/REDUCTION MEASUREMENT

CROSS REFERENCE TO RELATED APPLICATION

This application is a continuation-in-part of PCT Application No. PCT/US11/38124, filed on May 26, 2011, entitled "Fluid Quantification System and Method", the disclosure of which is incorporated herein by reference.

BACKGROUND

Liquids may be treated or processed by the addition of oxidizers for performing a disinfection process. One example is water treatment. Oxidizer materials may be added to water in order to destroy or kill organic and biological materials in the water. Oxidizer materials for use in water treatment may include but are not limited to chlorine, chlorine dioxide, monochloramine, hypobromous acid, hydrogen peroxide, potassium permanganate, and oxygen/ozone.

A typical stage in a water treatment process comprises adding chlorine (or any other suitable oxidizer), with the added chlorine reacting with dissolved contaminants and disinfecting the water. For waste water treatment processes or other treatment involving discharge into natural water bodies (for example, ballast water treatment), this is followed by a de-chlorination stage to remove excess or remaining oxidant. The dechlorination process may comprise adding reducing agents such as $SO_2$, $HSO_3^-$, and $SO_3^{2-}$ into chlorinated water to consume any residual chlorine/oxidizer. The final stage comprises measuring the oxidant residual level in the water to ensure that oxidizer levels are within desired bounds or permitted amounts.

Typically, government regulations specify a maximum or acceptable level of oxidizing materials that may remain in treated water, such as drinking water or wastewater final effluent. Consequently, municipal water treatment processes may require testing in order to ensure that oxidizing materials have been sufficiently removed and to ensure regulatory compliance.

Chlorine measurement in water is often achieved through batch processing, with the measuring comprising obtaining a water or liquid sample, adding a chemical reactant to the sample, waiting a known time period for the chemical reactant to react with available chlorine, and measuring the amount of remaining chlorine.

BRIEF SUMMARY

In summary, one aspect provides an oxidation/reduction system, comprising: one or more reference sensors configured to generate intermittent oxidizer/reducer reference measurements; one or more corroboration sensors configured to generate one or more substantially continuous oxidizer/reducer-related measurements; and meter electronics in communication with the one or more reference sensors and the one or more corroboration sensors; wherein the meter electronics are configured to process the one or more substantially continuous oxidizer/reducer-related measurements with the intermittent oxidizer/reducer reference measurements to generate substantially continuous representative oxidizer/reducer measurements.

Another aspect provides an oxidation/reduction system, comprising: a reference sensor configured to generate intermittent oxidizer/reducer reference measurements; a pH sensor configured to generate substantially continuous pH measurements; an oxidation-reduction potential (ORP) sensor configured to generate substantially continuous ORP measurements; and meter electronics in communication with the reference sensor, the pH sensor, and the ORP sensor; wherein the meter electronics are configured to process the one or more substantially continuous ORP measurements and substantially continuous pH measurements with the intermittent oxidizer/reducer reference measurements to generate substantially continuous representative oxidizer/reducer measurements.

A further aspect provides an oxidation/reduction quantification method, comprising: receiving intermittent oxidizer/reducer reference measurements from one or more reference sensors; receiving one or more substantially continuous oxidizer/reducer-related measurements from one or more corroboration sensors; and processing the one or more substantially continuous oxidizer/reducer-related measurements with the intermittent oxidizer/reducer reference measurements to generate substantially continuous representative oxidizer/reducer measurements.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to be limiting, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details and examples are provided to give a thorough understanding of embodiments. One skilled in the relevant art will recognize, however, that various embodiments can be practiced without one or more of the specific details, or with other methods, components, materials, et cetera. In other instances, well-known structures, materials, or operations are not shown or described in detail. The following description is intended only by way of example, and simply illustrates certain example embodiments.

A drawback to a conventional chemical reactant test for oxidation/reduction quantification is the elapsed time required in order to produce a result. Chemical tests produce accurate results, but require noticeable periods of time to achieve (on the order of minutes). For example, a typical chlorine measurement may take several minutes to complete. During this time, the liquid content may have changed, such as where the liquid being tested is an outflow of a treatment process. A conventional measurement will therefore comprise a measurement of an oxidizer material level from a past time period and may not reflect current liquid conditions.

As a result, the testing may not be accurate or even representative. The resulting measurement values may be relatively incomplete. Such periodic measurements may be inadequate when conditions are rapidly changing. Even moderate changes in oxidizer material levels may not be captured by such measurements. The result of using a conventional test may be violation of oxidizer/reducer regulations, an over-use of oxidizer or reducer materials, resulting in undue cost, under-use of oxidizer or reducer materials and/or undesirable or unhealthy levels of oxidizer/reducer materials remaining in the liquid, including a toxic effect on aquatic life if treated water is released into rivers or lakes.

It is desired that oxidizers and/or reducers in a liquid be accurately and reliably measured in order to prevent contamination, prevent regulatory violations, and minimize the cost of additives. Accordingly, an embodiment provides for rapid testing, suitable for situations in which water qualities may be changing rapidly, such as for example where there is fluid flow.

An embodiment provides conventional, highly accurate measurement of an oxidizer in solution (referred to herein as a reference measurement), provides rapid and/or continuous estimated measurements of an oxidizer in a solution (referred to herein as corroboration or related measurements), and may combine these two measurement sources to produce a substantially continuous, accurate measurement or estimate of oxidizer/reducer levels in solution (referred to herein as representative oxidizer/reducer measurements), even in situations where solution characteristics may be rapidly changing, such as in water plant outflow testing.

The description now turns to the figures. The example embodiments will be best understood by reference to the figures. The following description is intended only by way of example, and simply illustrates certain example embodiments.

Figure 1:
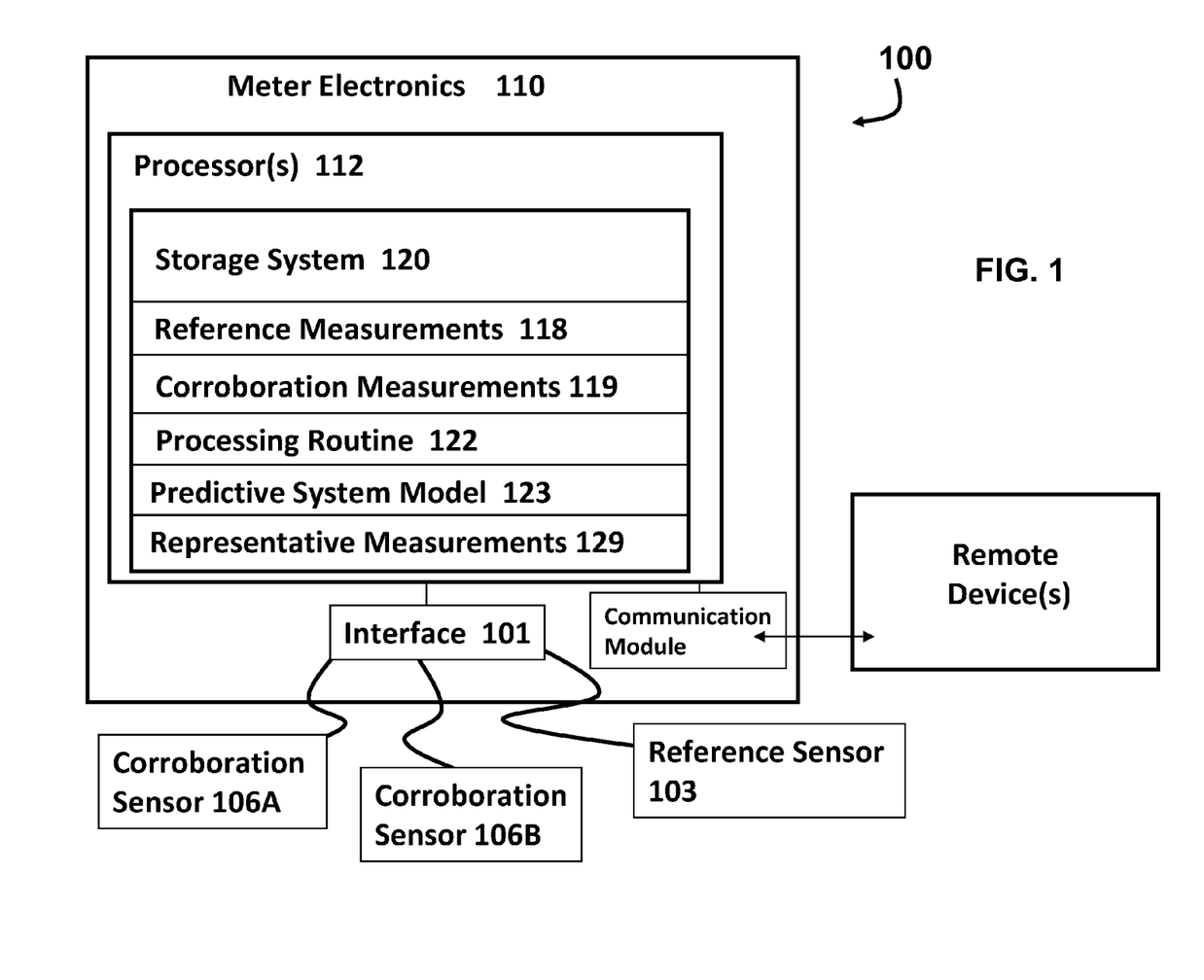
FIG. 1 illustrates an example oxidation/reduction system.

Referring to FIG. 1 an embodiment provides an oxidation/reduction instrument 100 that may employ a predictive system model 123 (which may include a Kalman filter, as further described herein, which may include both a state transition model and a measurement prediction model) as part of processing the oxidizer/reducer measurement data. The predictive system model 123, which may comprise an unscented Kalman filter, can provide a prediction of measurement data, with the predicted measurement data serving as representative measurement values in the time periods between actual measurement data, that is, in time periods between the intermittent oxidizer/reducer reference measurements. An embodiment thus provides a state estimate that is updated based on one or more new measurements, where the new measurements may be a reference measurement, a related measurement, or both, as further described herein. The state estimate may be updated on receipt of new measurement data.

Processor(s) 112 in some embodiments receive the intermittent oxidizer/reducer reference measurements and the one or more substantially continuous oxidizer/reducer-related measurements and process these measurements to generate substantially continuous representative oxidizer/reducer measurements. In at least one embodiment, the one or more substantially continuous oxidizer/reducer-related measurements are used to update a state estimate and a covariance matrix of the predictive system model 123. The one or more substantially continuous oxidizer/reducer-related measurements may include at least an oxidation-reduction potential (ORP) measurement signal and a pH measurement signal that can be used to generate the representative oxidizer/reducer measurements in the time periods between the intermittent oxidizer/reducer reference measurements.

A predictive system model 123 utilized may be based on an unscented Kalman filter. Unscented Kalman filters have previously been used in other applications, such as tracking of ballistic and orbital objects, for example as may be used in determining velocity and direction of flight. Conventional Kalman filters have also been used to track plant dynamics in, for example, chemical manufacturing. The unscented Kalman filter has typically been used to refine and improve velocity measurements of a solid object moving at very high speeds. The unscented Kalman filter has been applied to flow estimation, as for example described in PCT Application No. PCT/US11/38124, incorporated by reference here.

The oxidation/reduction instrument 100 includes meter electronics 110, at least one reference sensor 103 and one or more corroboration sensors 106A-106B coupled to the meter electronics 110 via one or more corresponding cables or other signal transmission apparatus (wired or wireless). The meter electronics 110 communicates with the reference sensor 103 and the one or more corroboration sensors 106A-106B. In some embodiments, the meter electronics 110 and the sensors 103 and 106A-106B may comprise an integrated instrument device. Alternatively, other embodiments may be implemented in a modular system, where different components of the overall "instrument" 100 are functionally interrelated. For example, in an example embodiment the meter electronics 110 may be remotely located from the sensors 103 and 106A-106B, such as in a monitoring station, data accumulation station, server, et cetera. Similarly, in some embodiments, meter electronics 110 may communicate with other remote device(s), either via wired or wireless connection.

The oxidation/reduction instrument 100 generates a measurement of oxidizers/reducers in the liquid. More specifically, the oxidation/reduction instrument 100 can measure the amount of oxidizers/reducers in treated water, such as the concentration of chlorine or other oxidizers in the liquid. The reference sensor 103 and the one or more corroboration sensors 106A-106B generate measurements that are manipulated and combined (or otherwise processed) to generate substantially continuous representative oxidizer/reducer measurements. The substantially continuous representative oxidizer/reducer measurements may not be directly obtained. The representative oxidizer/reducer measurements may be generated in time periods between the intermittent oxidizer/reducer reference measurements.

The reference sensor 103 may directly measure an oxidizer/reducer level in the liquid to be monitored. The reference sensor 103 may generate intermittent oxidizer/reducer measurements for the liquid. The reference sensor 103 can comprise a batch instrument that performs a chemical reaction test. The reference sensor 103 can comprise an instrument that requires a measurable period of time in order to generate an oxidizer or reducer measurement. The reference sensor 103, because it requires time in order to generate an accurate measurement, may not produce instantaneous measurements and may not produce continuous measurements. For example, for measurements of chlorine, the reference sensor 103 in some embodiments may be capable of producing oxidizer/reducer measurements about every two and a half minutes.

The one or more corroboration sensors 106A-106B generate oxidizer/reducer-related measurements for the liquid. The one or more corroboration sensors may rapidly generate one or more substantially continuous electronic measurement signals. The one or more substantially continuous electronic measurement signals comprise substantially continuous oxidizer/reducer-related measurement signals.

The one or more corroboration sensors 106A-106B may not generate direct oxidizer/reducer measurements. However, the one or more corroboration sensors 106A-106B can be used to complement the direct oxidizer/reducer measurements that are produced by the reference sensor 103. Similarly, the reference sensor 103 can be used to verify the oxidizer/reducer-related measurements that are generated by the one or more corroboration sensors 106A-106B.

The meter electronics 110 includes an interface 101 and processor(s) 112 coupled to the interface 101. The interface 101 is configured to receive the intermittent oxidizer/reducer reference measurements from the reference sensor 103 and can receive the one or more substantially continuous oxidizer/reducer-related measurements from the one or more corroboration sensors 106A-106B and can relay the signals to the processor(s) 112. In addition, the interface 101 can perform any manner of pre-processing operations, such as digitizing the one or more raw fluid measurements, for example. The interface 101 can further perform any manner of pre-amplification or pre-filtering, as desired. Alternatively, the amplification or other pre-processing can be performed in a respective sensor.

The meter electronics 110 may further include a storage system 120. The storage system 120 can comprise a component of processor(s) 112, as shown, or can comprise a separate component or components. The storage system 120 can include reference measurements 118 and corroboration measurements 119. The reference measurements 118 are intermittent oxidizer/reducer reference measurements received from the reference sensor 103. The corroborations measurements 119 are substantially continuous oxidizer/reducer-related measurements received from the one or more corroboration sensors 106A-106B. The storage system 120 can further include processing routine 122, a predictive system model 123, and representative oxidizer/reducer measurements 129, which are the produced representative oxidizer/reducer measurements.

The meter electronics 110 may be further configured to compare one or more elements of the predictive system model 123 to one or more corresponding thresholds and perform one or more corrective actions if the one or more elements do not satisfy the one or more corresponding thresholds. Similarly, the reference measurement(s), the related measurement(s), and/or the representative measurement(s) may be compared to corresponding threshold(s), and corrective action(s) may be taken responsive to exceeding threshold(s).

For example, a comparison may detect an oxidizer/reducer level that exceeds a threshold. A corrective action can comprise controlling the addition of chlorine (or other oxidizer) to the liquid, controlling the addition of a reducer for the removal of oxidizer from the liquid, generating an alarm if the oxidizer/reducer level exceeds a threshold, adjusting the calibration parameters of a corroboration sensor or sensors, and/or providing hardware maintenance and calibration suggestions to the operator or user. These corrective actions are non-limiting examples.

Because an oxidation-reduction reaction involves an exchange of electrons, it can generate measurable electric currents. The generated electrical current can be measured and used to quantify the amount of oxidizers/reducers in the liquid. The type and amount of reductants (reducers) and oxidants (oxidizers) present in a water system directly impact ORP measurements, and can greatly change the water quality of an aqueous system.

The concentration of hydrogen ions (pH) may also define the chemical form of oxidizers/reducers, and therefore may affect the measured ORP voltage. Therefore, by acquiring both pH measurements and ORP measurements, the generated hydrogen ion electrical current can be taken into account to more accurately determine oxidizer/reducer levels using the ORP measurements. Consequently, the pH measurements can be used to verify whether ORP measurement changes are due to changes in oxidation-reduction reactions, are due to changes in pH, or both.

Figure 2:
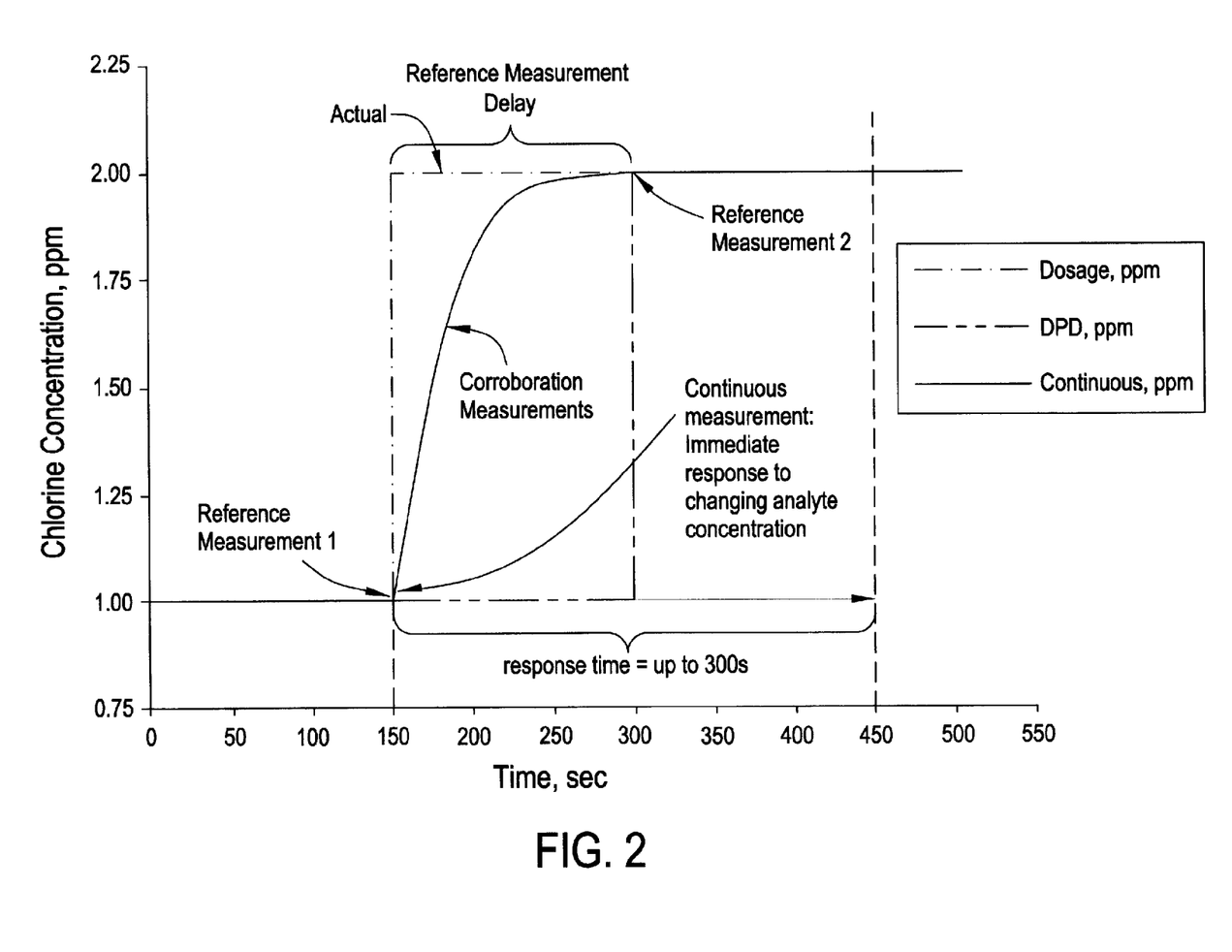
FIG. 2 illustrates example oxidizer/reducer measurement response times.

FIG. 2 is a graph of oxidizer/reducer measurement response in the oxidation/reduction instrument 100 according to an embodiment of the invention. The actual (dosage) oxidizer/reducer concentration (chlorine concentration in parts-per-million (PPM) in this example) may increase rapidly as indicated. The reference measurements (for example, DPD (N,N-diethyl-p-phenylenediamine) measurements) made by the reference sensor 103 illustrate a possible lengthy delay between an oxidizer/reducer change and an accurate and reliable measurement by the reference sensor 103 (that is, the delay between reference measurements 1 and 2). Thus, reference measurements occur intermittently and/or periodically (once every 150 seconds in the example illustrated). The substantially continuous corroboration measurements made by the one or more corroboration sensors 106 begin to change essentially as soon as the oxidizer/reducer concentration changes. Thus, the reference measurements alone involve a delay. The delay time may depend on when the change in concentration occurs with respect to the intermittent reference measurements, but may be upwards of 300 s if reference measurements are spaced at 150 s intervals, as illustrated in FIG. 2.

Figure 3:
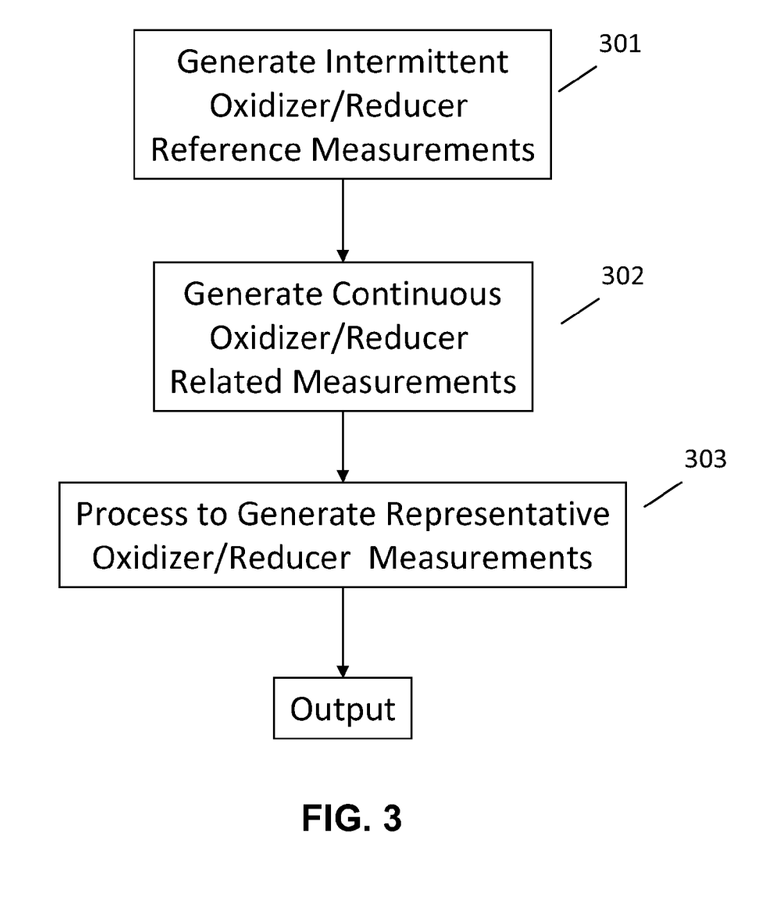
FIG. 3 illustrates an example method for oxidation/reduction measurement/quantification.

FIG. 3 is a flowchart of an example oxidation/reduction quantification method according to an embodiment. In step 301, intermittent oxidizer/reducer reference measurements are generated. The intermittent oxidizer/reducer reference measurements may be generated by an oxidizer/reducer reference sensor 103. The reference sensor 103 can comprise a device for accurately measuring oxidizer/reducer levels in a liquid and/or a batch instrument that performs a chemical reaction test.

The reference sensor 103, because it may require substantial time in order to generate a measurement, may not produce instantaneous or continuous measurements, but rather intermittent oxidizer/reducer measurements. For example, for measurements of chlorine, the reference sensor 103 in some embodiments may be capable of producing oxidizer/reducer measurements about every two and a half minutes. However, the period between measurements may depend on the nature and operation of the reference sensor 103.

Chlorine measurement in water is achieved through batch processing, with the measuring comprising the reference sensor 103 obtaining a water or liquid sample, adding a chemical reagent or reagents to the sample, waiting a known time period for the chemical reactant to react with available chlorine, and measuring the amount of chlorine/oxidizer using the reaction. However, other measurement/quantification methods are contemplated and are within the scope of the description and claims.

The intermittent oxidizer/reducer reference measurements are typically very accurate and reliable for monitoring and logging of oxidizer/reducer levels. However, it is a drawback that the reference sensor 103 may not instantaneously and/or continuously generate oxidizer/reducer measurements.

In step 302, one or more substantially continuous oxidizer/reducer-related measurements are generated by one or more corroboration sensors 106A-106B, for example as one or more substantially continuous electronic measurement signals. The one or more corroboration sensors 106A-106B may not generate oxidizer/reducer measurement signals that are as accurate as measurements produced by the reference measurement sensor 103. The continuous measurements may not be direct. However, the one or more corroboration sensors 106A-106B are included to generate signals that are related to the oxidizer/reducer levels. The one or more corroboration sensor signals may be used to infer the oxidizer/reducer levels, to predict future values or trends, and/or to detect changes in the oxidizer/reducer levels via modeling. The one or more corroboration sensors 106A-106B may be calibrated against the reference sensor 103. As a result, the one or more corroboration sensor signals may be used to generate approximate oxidizer/reducer values with sufficient accuracy in the times between the intermittent oxidizer/reducer reference measurements to produce representative oxidizer/reducer measurements 303.

The one or more corroboration sensors 106A-106B may comprise electrochemical sensors that generate electrical measurement signals. The one or more corroboration sensors 106A-106B may interact with the liquid and generate the electrical measurement signals by quantifying materials in the liquid. In one embodiment, the one or more corroboration sensors 106A-106B include a pH sensor and an ORP sensor. The pH sensor generates an electrical signal wherein the voltage level of the electrical signal varies according to the pH of the liquid. The ORP sensor generates an electrical signal wherein the voltage level of the electrical signal varies according to the amount of oxidizer/reducer in the liquid or according to oxidation-reduction reactions occurring in the liquid.

The use of the one or more corroboration sensor signals to generate oxidizer/reducer values in between reference measurements is possible even though the one or more corroboration sensor signals are not direct oxidizer/reducer measurements. For example, chlorine and other water disinfection compounds function by oxidation of organic and biological material in the water, that is, through oxidation-reduction reactions. As a result, the ORP measurement will change with changes in oxidizer/reducer levels in the water. The ORP measurement will react substantially immediately to an increase in chlorine concentration. The ORP measurement may not react as quickly to a decrease in chlorine, but a drop in the chlorine level is normally of much less concern than an increase in chlorine level for certain applications.

The pH measurement can be used to verify that a change in the ORP measurement is due to a change in oxidizer/reducer levels. The pH measurement can be used to verify that a change in the ORP measurement is not due to a change in the oxidizer/reducer form. For example, chlorine may be used in a hypochlorous acid form or a hypochlorite ion form. Hypochlorous acid is typically prevalent at a pH of about 6.5, while hypochlorite ion is typically prevalent at a pH of about 8.5. These two chlorine species have substantially different oxidation-reduction potential, which can affect the voltage generated by the ORP sensor. Consequently, a change in pH may indicate a change in the form of the oxidizer, wherein the pH measurement may be used to interpret the ORP measurement. As a result, if the ORP measurement changes while the pH measurement does not change, then it can be concluded that the form of the oxidizer/reducer has not changed. Conversely, if both the ORP measurement and the pH measurement change, then the form of the oxidizer/reducer may have changed. Consequently, the pH measurement is used to verify and/or complement the ORP measurement.

In step 303, the intermittent oxidizer/reducer reference measurements are processed with the substantially continuous oxidizer/reducer-related measurements to generate substantially continuous representative oxidizer/reducer measurements. The one or more substantially continuous corroboration measurements may be produced in between the intermittent oxidizer/reducer reference measurements and used to verify or interpolate to a current oxidizer/reducer level, based on the intermittent oxidizer/reducer reference measurements. Thus, where reference measurements require a significant length of time to obtain, the predictive system model can extrapolate trends and measurement values between reference (direct/actual) measurement occurrences.

As described herein, a representative oxidizer/reducer measurement can be compared to a threshold value and used to detect an oxidizer/reducer level that is out of bounds. The representative oxidizer/reducer measurement can be used to generate an alarm if the oxidizer/reducer level is out of bounds, and/or can be used to adjust the calibration parameters of a corroboration sensor or sensors 106A-106B. Alternatively, one of the intermittent oxidizer/reducer reference measurements can be used to adjust the calibration parameters of the corroboration sensors 106A-106B. The representative oxidizer/reducer measurement can be used to provide a maintenance or calibration suggestion to the operator or user.

As an example of modeling a system state to provide a substantially continuous representative measurement of oxidizer levels in a solution, the description now focuses on specific oxidizers/reducers in water treatment. It should be apparent to those having ordinary skill in the art, however, that these are non-limiting examples.

Chlorine Estimation Example

An embodiment provides for combining non-real-time reference sensor measurements with one or more electrochemistry corroboration sensor measurements to obtain reliable real-time estimates of total chlorine residuals. An example reference sensor 103 is a Hach CL17 total chlorine analyzer. Real-time electrochemical measurements may be gathered from corroboration sensors 106A-106B, such as measurements obtained from (at least in part) an ORP sensor, possibly augmented by pH and temperature sensing (both available in one probe).

The reference sensor 103 may use an EPA-accepted method that allows for regulatory reporting of total chlorine residuals at a minimum 2.5 minute interval. ORP, pH, and fluid temperature can be read essentially instantaneously. An example of how to correlate these real-time corroboration sensor 106A-106B measurements with periodic measurements from a reference sensor 103 so that reliable estimates of total chlorine concentration are available in real time will now be described. Again, although the following examples are focused on the context of monitoring chlorine residuals, those having ordinary skill in the art should understand that similar methods may be used to monitor the total residual concentration of other chemicals, oxidants, et cetera, depending on the measurements available and the application at hand.

Process Dependence of Total Chlorine

Corroboration (ORP) sensors 106A-106B may be affected by a multiplicity of aqueous species, but in dechlorination processes the primary ones are free chlorine and various chloramines Free chlorine consists of hypochlorous acid (HOCl) and hypochlorite ion (OCl⁻). The chloramines are primarily monochloramine ($NH_2Cl$) and dichloramine ($NHCl_2$) (the other known chloramines may be disregarded due to their low concentration and the fact that they are unlikely to appear or affect the process). Total chlorine concentration is then given by:

$$Cl_{TOT} = HOCl + OCl^- + NH_2Cl + NHCl_2$$

Figure 4:
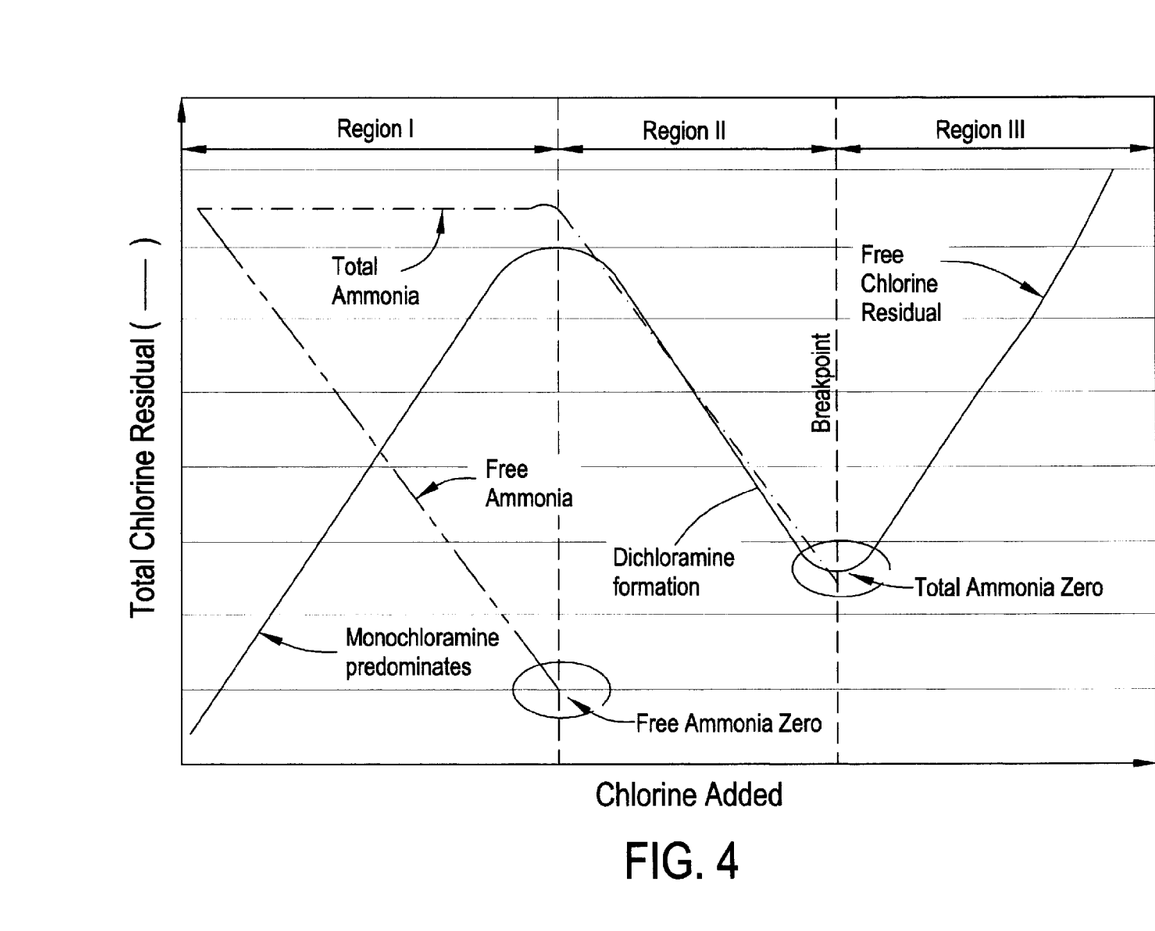
FIG. 4 illustrates total chlorine residual versus chlorine added in an example water treatment process.

Typically, only one or two species are present at once. FIG. 4 illustrates how the relative concentrations vary as more chlorine is added to the process where ammonia is present.

Region I typically occurs for $Cl_2$:N<5:1, and is characterized by presence of free ammonia in the process of its reaction with added chlorine, which is called chloramination. The result is increasing concentrations of monochloramine. For example, this reaction occurs upstream in the wastewater treatment process. At the point of dechlorination, free ammonia has normally been driven to zero, and the process is operating in either Region II or Region III.

Region II begins when enough chlorine has been added to bind all free ammonia. Typically this happens when $Cl_2$:N=5:1. As more chlorine is added, monochloramine is converted to dichloramine, or it may be further oxidized to nitrogen trichloride ($NCl_3$) with associated release of nitrogen gas. The monochloramine/dichloramine equilibrium depends strongly on the process pH. Therefore, Region II is characterized by a mixture of $NH_2Cl$ and $NHCl_2$ species. Free chlorine reacts with either species, so it may be assumed that free chlorine is negligible as long as chloramines are present. Once these have been consumed, the free chlorine concentration begins to rise ("break point"), and the process enters Region III.

Figure 5:
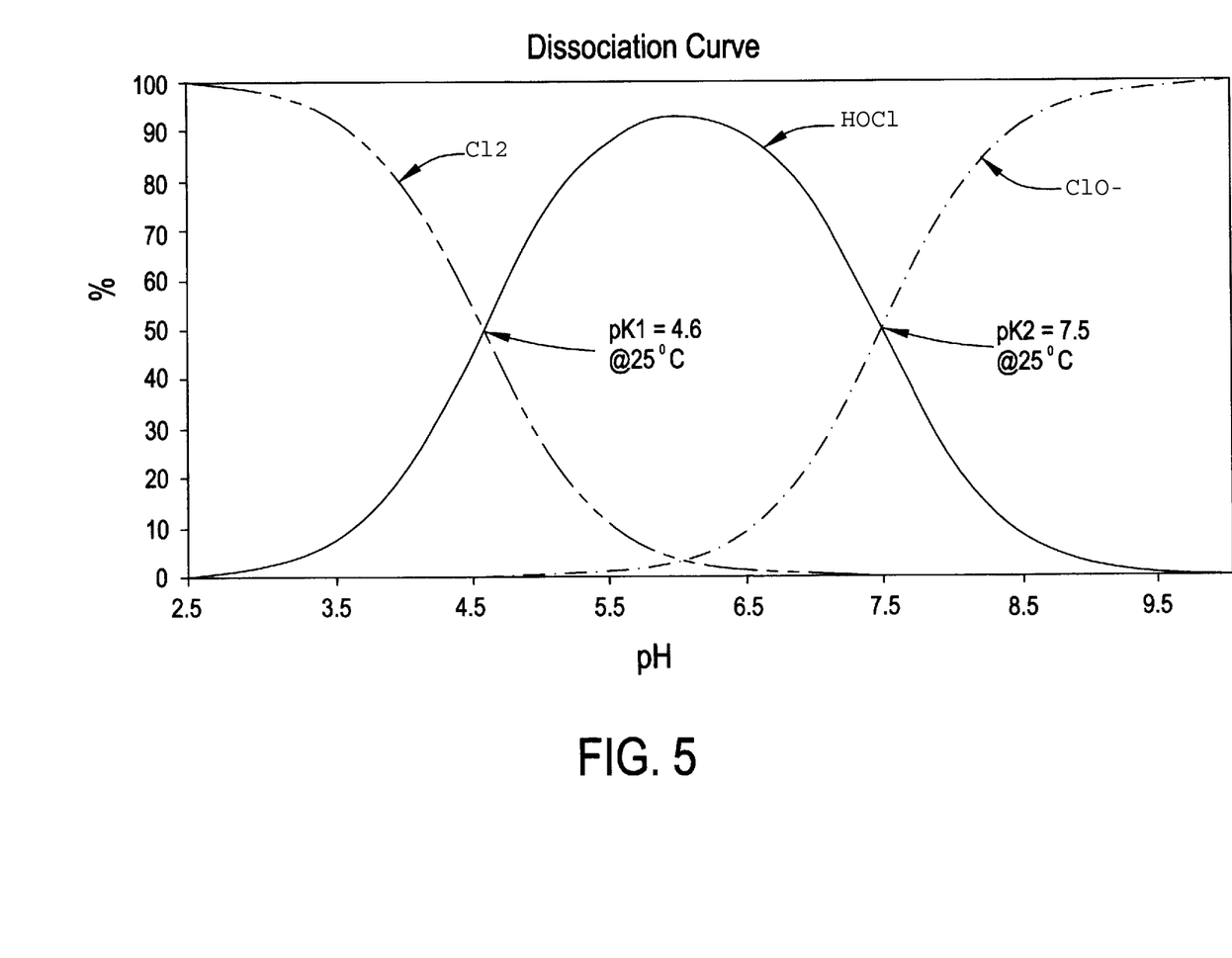
FIG. 5 illustrates a chlorine dissociation curve.

Region III is characterized by rising levels of free chlorine. A break point typically occurs when $Cl_2$:N>9:1. Free chlorine consists of both HOCl and its dissociation product, OCl⁻. These species are present in equilibrium concentrations that depend on pH. At a pH of 7.5, their relative fractions are about 1:1, as illustrated in FIG. 5.

In a wastewater disinfection application, discharge of residual disinfectant is regulated. Therefore, plants destroy the residual chlorine in a dechlorination chamber downstream. Since the wastewater always contains ammonia load, the chlorination normally goes through the steps displayed in FIG. 4, though only total chlorine concentration (without speciation) is monitored to control this process. Typically the pH is held around 7.5 to 8.0 because this reduces formation of dichloramine, which has a noxious odor, and disinfection byproducts (DBP's).

ORP Prediction Models for Total Chlorine

An embodiment provides a way to predict the measured ORP at any point in the process diagram presented in FIG. 4. Since there are three distinct regions, there will be three prediction equations. To the extent that these produce significantly different predictions, it may be important to know which to use. Distinguishing between Region II and Region III may be particularly difficult.

Region I Model

Figure 6:
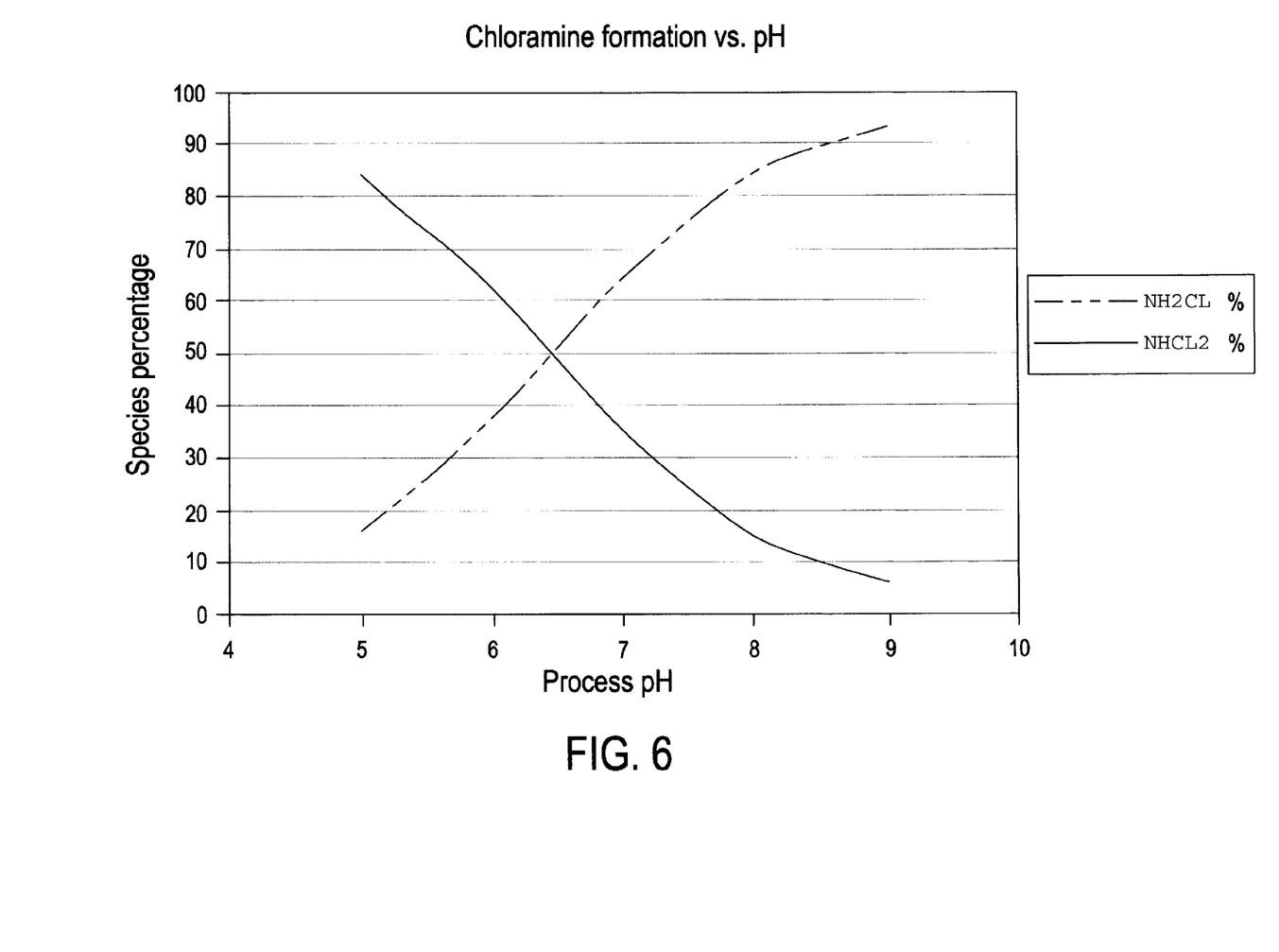
FIG. 6 illustrates chloramine formation versus pH.

It may be assumed that monocholoramine is the predominant chlorine species in Region I. The presence of free ammonia assures this in two ways: first, by quickly reacting with free chlorine as it is added, and second by raising the pH, so that the primary product of that reaction is $NH_2Cl$ rather than $NHCl_2$, as illustrated in FIG. 6. So for practical purposes, $Cl_{TOT}=NH_2Cl$. The ORP response obeys a Nernst equation of the form:

$$ORP = E_0 + C_I T \ln(NH_2Cl) \tag{0.1}$$

where $E_0$ is an electrode offset, and $C_I$ is a slowly-changing slope constant which will be learned from process observation. Substituting total chlorine for monochloramine and solving, the Region I fast update equation is obtained:

$$Cl_{TOT} = \exp\left(\frac{ORP - E_0}{C_I T}\right). \tag{0.2}$$

In typical use, $E_0$ may be obtained from periodic calibration, and $C_I$ may be updated by a Kalman filtering algorithm so that the predictions of equation (0.2) match readings from the reference sensor. In contrast to a one-time calibration, real-time update of the slope allows local approximation of an electrode response characteristic which is either not precisely linear, or which has changed due to aging and/or fouling.

Region II Model

In Region II, both monochloramine and dichloramine may be present, with their relative percentages depending on pH, as shown in FIG. 6. Although many plant operators seek to minimize formation of dichloramine by keeping their process pH above 8, some dichloramine is still present.

Predicting ORP readings for various chloramine mixtures is complex. FIG. 6, empirically derived, shows that both species are present in the region 4<pH<8, which makes the ORP electrode potential difficult to predict. Even for pH>8, where the main product is monochloramine, it results from two distinct reactions involving different ammonia species: molecular ammonia ($NH_3$) and ammonium ion ($NH_4^+$), with the former predominating for pH<8.75 and the latter predominating when pH>9.75. At intermediate pH values, both species are present. The relative concentrations can be calculated as described herein.

Ammonia in solution dissolves according to:

$$NH_3 + H_2O \underset{K_b}{\rightleftharpoons} NH_4^+ + OH^- \quad \text{where} \tag{0.3}$$

$$K_b \equiv \frac{[NH_4^+][OH^-]}{[NH_3]} = 1.774 \times 10^{-5}. \tag{0.4}$$

The dissociation of water is characterized by:

$$K_w \equiv [H^+][OH^-], \tag{0.5}$$

which depends on temperature, but has a typical value of $K_w = 1.008 \times 10^{-14}$. Rearranging the definition of pH yields:

$$[H^+] = 10^{-pH}. \tag{0.6}$$

Combining the previous three equations, the ratio of ammonia ion to molecular ammonia concentration may be calculated. The result depends on pH:

$$\frac{[NH_4^+]}{[NH_3]} = \frac{K_b}{K_w} \cdot 10^{-pH}. \tag{0.7}$$

This ratio is approximately 1 at pH=9.25.

Two important paths of monochloramine creation are now described. Assuming an alkaline process pH, the reaction involving $NH_3$ is:

$$NH_3 + OCl^- \rightleftharpoons NH_2Cl + OH^-, \quad (0.8)$$

and the reaction involving $NH_4^+$ is:

$$NH_4^+ + OCl^- \rightleftharpoons NH_2Cl + H_2O. \quad (0.9)$$

Experiments have shown that equilibrium potentials for monochloramine below pH=8.75 change by −75 mV/pH. Above pH=9.75, the slope is −41 mV per pH. It is noteworthy that in the original experiments, dichloramine formation was minimized by maintaining an excess of $NH_3$, a situation that does not obtain in Region II. No similar results are known for dichloramine. It would likely be possible to experimentally determine such a curve below pH=4, but this highly acidic pH range is of little interest for water treatment in general and dechlorination processes in particular.

Assuming equilibrium potential curves for both $NH_2Cl$ and $NHCl_2$ were known, it might seem that the ORP reading could be predicted by superposition. Unfortunately, this is not the case. Considered individually, each species produces an electrode response having the general form:

$$ORP = E'_0 + C_{II}T\ln\left(\frac{\text{oxidized species } conc.}{\text{reduced species } conc.}\right). \quad (0.10)$$

This leads to difficulty, because adding a second chloramine species will cause the relative concentrations above to shift.

It follows that exact prediction of ORP vs. pH in Region II remains elusive. In designing a monitoring algorithm, one might assume that ORP in Region II obeys a rule of the form:

$$ORP = E'_0 + f(pH) \cdot C_{II}T\ln(Cl_{TOT}), \quad (0.11)$$

in which f(pH) is an empirical function that encapsulates the pH-dependent speciation and its resulting effect on the electrode slope. In the formulation above, f(pH) is written as though it is process and temperature independent, which may or may not be true.

Another approach would be to deal with the speciation problem head-on, by adding a sensor capable of distinguishing monocholoramine from dichloramine Knowing relative species concentrations still leaves the electrode response problem unresolved, but the result can be expressed formally as:

$$ORP = E'_0 + f\left(\frac{NH_2Cl}{NHCl_2}\right) \cdot C_{II}T\ln(Cl_{TOT}). \quad (0.12)$$

Either way, a Region II fast update equation would then have the form:

$$Cl_{TOT} = \exp\left(\frac{ORP - E'_0}{f(\cdot)C_{II}T}\right). \quad (0.13)$$

In the remainder of the description, the simplifying assumption that the plant operator keeps the process pH above 8, causing monochloramine to be the dominant species in Region II, just as in Region I, is made. This allows:

$$ORP = E'_0 + C_{II}T\ln(NH_2Cl) \quad (0.14)$$

and $$Cl_{TOT} = \exp\left(\frac{ORP - E'_0}{C_{II}T}\right), \quad (0.15)$$

which have the same form as equations (0.1) and (0.2).

Region III Model

In Region III, total chorine consists of some combination of HOCl and OCl⁻. These two species appear on opposite sides of the following dissociation equation:

$$HOCl \rightleftharpoons H^+ + OCl^-. \quad (0.16)$$

Other hydronium ions may be present in solution, so the equilibrium position depends on pH. The relative concentrations of hypochlorous acid and hypochlorite ion may be expressed as:

$$\frac{OCl^-}{HOCl} = K_a \cdot 10^{pH}, \quad (0.17)$$

where $K_a = 29 \times 10^{-9}$. It follows that the relative concentrations are equal at a pH of about 7.5.

HOCl has a standard reduction potential of 1.48V compared to 0.81V for OCl⁻, so ORP response will be dominated by the concentration of HOCl:

$$ORP \approx E''_0 + C_{III}T\ln(HOCl). \quad (0.18)$$

ORP may be used as a surrogate for total chlorine by applying equation (0.17):

$$Cl_{TOT} = HOCl + OCl^- = HOCl \cdot (1 + K \cdot 10^{pH}). \quad (0.19)$$

This leads to the following equation for predicting the ORP reading from total chlorine concentration:

$$Cl_{TOT} = (1 + K_a \cdot 10^{pH})\exp\left(\frac{ORP - E''_0}{C_{III}T}\right). \quad (0.21)$$

Rearranging this, the fast update equation for Region III is obtained:

$$ORP = E''_0 + C_{III}T\ln\left(\frac{Cl_{TOT}}{1 + K_a 10^{pH}}\right). \quad (0.20)$$

At pH=8, $(1 + K_a \cdot 10^{pH})$ assumesa value of 3.9; at pH=9 its value is 30.

Generalized Model

Assuming that monochloramine dominates Region II, the ORP response and total chlorine prediction equations for Regions I and II have identical forms. For a given pH value, the corresponding Region III equations are also similar, except for the presence of an extra multiplicative factor. It may be assumed that $E_0'' = E'_0 = E_0$ because it is assumed that this offset is characteristic of the electrode rather than the process. So in general:

$$ORP = E_0 + CT\ln\left(\frac{Cl_{TOT}}{T(1 + K \cdot 10^{pH})}\right), \quad (0.22)$$

and $$Cl_{TOT} = (1 + K \cdot 10^{pH})\exp\left(\frac{ORP - E_0}{C \cdot T}\right).. \quad (0.23)$$

To match these functional forms with those for Regions I and II, take K=0. Equations (0.22) and (0.23) are highly nonlinear, and this is a reason for utilizing an unscented Kalman filter. A conventional Kalman filter is not suitable for this degree of non-linearity; however, it is worth noting that it may be possible to utilize a so-called extended Kalman filter. There is an advantage in having unified equations for all three operating regions: there is no longer a need to determine the region in which the plant is operating, just an estimate of the constants C and K based on the plant behavior.

Kalman Filtering

A Kalman filter has the ability to fuse information from multiple sensors and measurements to make statistically optimal estimates of one or more state variables. The unscented Kalman filter works with nonlinear systems. It has been applied to flow estimation, as for example described in PCT Application No. PCT/US11/38124, and the notation in the following description follows the notation used therein. Here, many details may be omitted in favor of focusing on those details that are unique to estimation of oxidant (chlorine in this non-limiting example) concentration.

Model Setup

The ORP offset is a property of the individual electrode and independent of time or operating region. If this is true, then $E_0$ can be determined by periodic offline calibration rather than including it in the state vector. The minimal state vector is then:

$$x_k = \begin{bmatrix} Cl_{TOT} \\ pH \\ T \\ C \\ K \end{bmatrix} \quad (0.24)$$

The subscript k is a discrete time index. The first three elements of the state vector should be understood to be "best estimates" of the corresponding process values at time k, they do not represent individual measurements.

The state transition model for a well-controlled process can be:

$$\underline{x}_k = \underline{x}_{k-1} + \underline{w}_k, \quad (0.25)$$

Comparing this to a canonical state transition model, the state transition matrix, $\underline{F}$, is simply an identity matrix. Per convention, $\underline{w}_k$ represents state noise, characterized by a noise covariance matrix, Q. The noise contribution cannot be predicted, so the state prediction equation is simply $\underline{x}_k = \underline{x}_{k-1}$, indicating that in the absence of new information it is expected that the system state will (on average) remain unchanged.

New information may be obtained very regularly in the form of periodic measurements from one or more corroboration (electrochemical) sensors 106A-106B (top three rows of the next equation), and less often as measurements from a reference sensor 103. Under the Kalman formalism, these are collected in a measurement vector. For the system, the measurement vector is:

$$\underline{y}_k = \begin{bmatrix} ORP \\ pH_{meas} \\ T_{meas} \\ Cl_{ref} \end{bmatrix} .. \quad (0.26)$$

Its final element, the chlorine reading from the reference sensor 103, is only available some of the time. When it is not available, the measurement vector is dimension 3 instead of dimension 4. Use of reduced-length measurement vectors is well documented in the literature and will not be further described herein.

For a given state, the measurement prediction equations are readily apparent. ORP is predicted according to equation (0.22). The other measurements are predicted by setting their a priori values equal to the corresponding state vector values.

Figure 7:
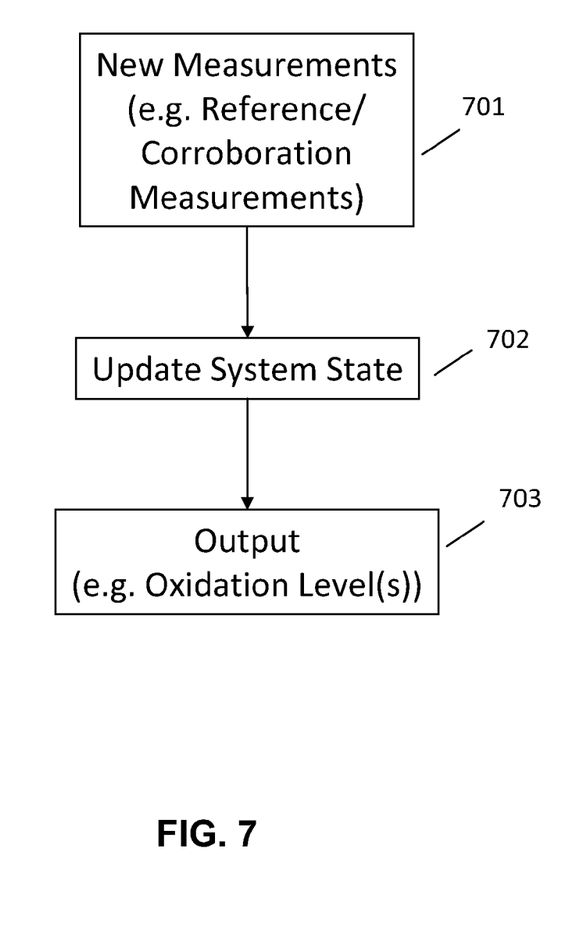
FIG. 7 illustrates an example method of using reference and corroborative sensor measurements to produce representative oxidizer/reducer measurements.

Referring generally to FIG. 7, when new measurements become available 701, a state update is done 702, and estimates/predictions regarding oxidant levels are made 703 based on the updated system state. For the most general case, this involves the procedures of an unscented Kalman filter. Certain covariance values are needed to accomplish this. The measurement noises can mostly be assumed to be independent, and initialized according to sensor data sheet values. One exception is that $T_{meas}$ is used to compensate $pH_{meas}$ based on Nernst's equation. Treating this rigorously requires some non-zero off-diagonal entries in the measurement covariance matrix. But for a process in which the temperature changes slowly relative to the measurement rate, this can be safely ignored.

The update process may be simplified by making a few well-founded assumptions. In particular, it may be assumed that the reference sensor 103 readings (when available) are actually correct, and don't need to be statistically filtered. This assumption is consistent with the fact that these readings are based on a standard method. So when $Cl_{ref}$ is available, one might simply set $Cl_{TOT} = Cl_{ref}$, irrespective of other measurements and irrespective of its previous value. This is equivalent to setting the measurement covariance entry associated with $Cl_{ref}$ very small relative to the other entries in the measurement covariance matrix. A complication is that $Cl_{ref}$ arrives later than needed. The following description explains how to handle this.

When $Cl_{ref}$ is not available, the system should use Kalman filtering sequential update to provide statistical filtering. The reason is not that the one distrusts the electrochemical measurements (though one might), but that one might not have perfect trust in the total chlorine predictions of equation (0.22). For instance, one needs to allow time for C and K to converge.

Out-of-Sequence Measurements

The Kalman filtering description herein suggests that the reference measurement value $Cl_{ref}$ could be substituted for $Cl_{TOT}$ when $Cl_{ref}$ happens to be available. The situation is actually more complicated, because reference measurements take a significant time to complete. For instance, if the reference sensor 103 is a Hach CL17, a "new" reading indicates what the total chlorine concentration was 2.5 minutes ago (or more), which may not be what it is now. This may be referred to as an "out-of-sequence" (OOS) measurement because by the time it arrives, there have already been a number of more recent electrochemical measurements. Suppose that N measurements of ORP, et cetera, are logged in the time it takes to complete one reference measurement. To properly utilize the reference measurement, a "back up" of the Kalman filtering algorithm to the time at which the reference sensor 103 grabbed its sample is needed, the resulting reference measurement may be applied to get an improved state estimate for that time, and the ORP and measurements taken since then may be re-applied to bring the revised state estimate up to the current moment.

Suppose L equally-spaced ORP measurements are taken for each reference sensor 103 measurement. Since electrochemistry readings are available on demand, it is reasonable to schedule them so that L will be an integer. A brute-force way to allow the so-called "retrodiction" of the Kalman filter is to buffer L prior measurement vectors $\underline{y}_k$, plus the vector $\underline{x}_{k-L}$ and the state covariance matrix $\underline{P}_x^+ (k-L)$. These are sufficient to allow the Kalman filter to be rerun from time index (k−L) when $Cl_{ref}(k-L)$ finally arrives. Due to symmetry of the covariance matrix, the total number of values that must be stored turns out to be 3L+25. Assuming reference sensor 103 measurements are taken every 2.5 minutes, and corroboration sensor 106A-106B measurements every second, L=150. If 32-bit floating-point values are stored, the total RAM space needed is less than 2 Kbytes.

Other work has given another solution to the OOS measurement problem that is different from that given above. Thus, other OOS measurement approaches may be utilized in connection with an embodiment in addition to the example approach explained herein depending on the use case encountered.

As will be appreciated by one skilled in the art, various aspects may be embodied as a system, method or program product. Accordingly, aspects may take the form of an entirely hardware embodiment or an embodiment including software that may all generally be referred to herein as a "circuit," "module" or "system." Furthermore, aspects may take the form of a program product embodied in one or more device readable medium(s) having device readable program code embodied therewith.

Any combination of one or more non-signal device readable medium(s) may be utilized. The non-signal medium may be a storage medium, such as a memory included in or associated with a microcontroller of a sensor or measurement instrument, for example storage system 120.

Program code embodied on a non-signal storage medium may be transmitted using any appropriate medium, including but not limited to wireless, wireline, optical fiber cable, RF, et cetera, or any suitable combination of the foregoing. Program code for carrying out operations may be written in any combination of one or more programming languages. The program code may execute entirely on a single device, partly on a single device, as a stand-alone software package, or partly on single device and partly on another device. In some cases, the devices may be connected through any type of connection, either a physical (wired connection, such as over a USB connection) or via a network, including a local area network (LAN) or a wide area network (WAN), or the connection may be made through other devices (for example, through the Internet using an Internet Service Provider).

Embodiments are described with reference to figures of methods, devices, and program products. It will be understood that portions of the figures can be implemented by program instructions. These program instructions may be provided to processor(s) of a programmable data processing device to produce a machine, such that the instructions, which execute via the processor(s) of the programmable data processing device create a means for implementing the functions/acts specified.

The program instructions may also be stored in a device readable storage medium that can direct a programmable data processing device to function in a particular manner, such that the instructions stored in the storage medium produce an article of manufacture including instructions which implement the function/act specified. The program instructions may also be loaded onto a programmable data processing device to cause a series of operational steps to be performed on the programmable device to produce a process such that the instructions which execute on the programmable device provide processes for implementing the functions/acts specified.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

We claim:

1. An oxidation/reduction quantification method, comprising:
   receiving intermittent oxidizer/reducer reference measurements from one or more reference sensors;
   receiving continuous oxidizer/reducer-related measurements from one or more corroboration sensors, wherein the continuous oxidizer/reducer-related measurements include continuous oxidation-reduction potential (ORP) measurements and continuous pH measurements; and
   combining the continuous oxidizer/reducer-related measurements with the intermittent oxidizer/reducer reference measurements to generate representative oxidizer/reducer measurements.

2. The method of claim 1, wherein the continuous oxidizer/reducer-related measurements include continuous temperature measurements.

3. The method of claim 2, wherein the continuous pH measurements substantially correspond to an oxidizer/reducer form.

4. The method of claim 1, wherein the representative oxidizer/reducer measurements are produced using a predictive system model.

5. The method of claim 4, wherein the predictive system model comprises an unscented Kalman filter.

6. The method of claim 4, further comprising:
   comparing one or more elements of the predictive system model to one or more corresponding thresholds; and
   performing one or more corrective actions if the one or more elements do not satisfy the one or more corresponding thresholds.

7. The method of claim 1, wherein the one or more reference sensors generate the intermittent oxidizer/reducer reference measurements using light absorbance.

* * * * *